United States Patent [19]

Grünbein et al.

[11] Patent Number: 4,465,880
[45] Date of Patent: Aug. 14, 1984

[54] PROCESS FOR THE MANUFACTURE OF METHYL CHLORIDE

[75] Inventors: Wolfgang Grünbein, Liederbach; Wilhelm Lendle, Bad Soden am Taunus; Hendrik W. Post, Hofheim am Taunus; Heinz Richter, Kronberg; Manfred Rossberg, Waldems, all of Fed. Rep. of Germany

[73] Assignee: Hoechst Aktiengesellschaft, Frankfurt am Main, Fed. Rep. of Germany

[21] Appl. No.: 257,395

[22] Filed: Apr. 24, 1981

[30] Foreign Application Priority Data

Apr. 26, 1980 [DE] Fed. Rep. of Germany ....... 3016220

[51] Int. Cl.³ .............................................. C07C 17/16
[52] U.S. Cl. .................................................. 570/258
[58] Field of Search ......................................... 570/258

[56] References Cited

U.S. PATENT DOCUMENTS

| | | | |
|---|---|---|---|
| 1,834,089 | 12/1931 | Carlisle | 570/258 |
| 1,920,246 | 8/1933 | Daudt | 570/258 |
| 2,442,285 | 5/1940 | Cheney | 570/258 |
| 3,484,494 | 12/1969 | Carson | 570/258 |
| 3,983,180 | 9/1976 | Habata et al. | 570/258 |

FOREIGN PATENT DOCUMENTS

| | | | |
|---|---|---|---|
| 1230743 | 5/1971 | United Kingdom | 570/258 |
| 1274150 | 5/1972 | United Kingdom | 570/243 |

*Primary Examiner*—Anton H. Sutto
*Assistant Examiner*—Joseph A. Boska
*Attorney, Agent, or Firm*—Curtis, Morris & Safford

[57] ABSTRACT

Methyl chloride is manufactured from methanol and hydrogen chloride in the gaseous phase in the presence of an aluminum oxide catalyst. The reaction is carried out in the presence of from 1 to 80 liters of oxygen per kg of methanol.

4 Claims, No Drawings

PROCESS FOR THE MANUFACTURE OF METHYL CHLORIDE

The invention relates to a process for the manufacture of methyl chloride by reaction of methanol with hydrogen chloride in the gaseous phase, in the presence of an aluminum oxide catalyst, at elevated temperature and under a pressure of at least 1 bar.

Similar processes are known, for example from U.S. Pat. Nos. 1,834,089, 1,920,246, Faith et al.: Industrial Chemicals (1957) 513–516, German Auslegeschrift No. 1,907,088, and Schlosser et al.: Chemie-Ingenieur-Technik 42 (1970), 1215–1219.

According to these methods, hydrogen chloride and methanol are introduced in gaseous and preheated form into a reactor, where the exothermal reaction proceeds in the presence of the catalyst according to the following scheme:

$$CH_3OH + HCl \rightarrow CH_3Cl + H_2O$$

The disadvantage of the state-of-the-art processes resides in the fact that the catalyst becomes inactive rather quickly and that simultaneously carbon precipitates. This inactivation manifests itself by increasing amounts of unreacted methanol leaving the reactor.

This inactivation is substantially accelerated when polychlorinated $C_1$- and $C_2$-hydrocarbons such as carbon tetrachloride, chloroform or tetrachloroethane are present in the reaction. Substances of this kind are often contained in industrial-grade hydrogen chloride obtained as a by-product in other processes, for example chlorinations.

It is the object of the invention to reduce the speed of catalyst inactivation and the precipitation of carbon.

The present invention resides in a process for the manufacture of methyl chloride by reaction of methanol with hydrogen chloride in the gaseous phase, in the presence of an aluminum oxide catalyst, at elevated temperature and under a pressure of a least 1 bar, which comprises carrying out the reaction in the presence of 1 to 80 liters of oxygen, as measured relative to 20° C. and 1 bar, per kg of methanol used.

The amount of oxygen (relative to 20° C. and 1 bar) is preferably from 1 to 50, especially 1 to 30, liters per kg of methanol.

The oxygen can be applied continuously or batchwise, in pure form or in that of an oxygen-containing gas, especially as air.

The reaction may be carried out in a reaction tube packed with the catalyst. However, a reactor consisting of a multitude of such tubes arranged in a bundle and cooled from the outside is preferably used. For cooling, the tube bundle is advantageously wrapped by a jacket through which a cooling medium flows.

During the reaction, a temperature profile establishes itself in the catalyst packing of the tubes, that is, the temperature rises first to a maximum directly after the reactor inlet, and decreases then in the direction of the reactor outlet due to the cooling. By means of the cooling, the temperature in the catalyst packing is generally adjusted in a range of from 250° to 500° C., preferably 300° to 320° C.

The reaction is carried out under a pressure of at least 1 bar, preferably 1 to 11, and especially 1 to 5, bar.

The aluminum oxide catalyst has preferably a specific surface of 120 to 200 m$^2$/g; it may be grainy or consist of shaped particles. Balls or cylinders are suitable catalyst shapes.

The molar ratio of methanol to hydrogen chloride is preferably from 0.75:1 to 1:1. When hydrogen chloride-containing polychlorinated $C_1$- and $C_2$-hydrocarbons are to be used for the reaction, it is recommended to keep the concentration of these compounds below 5, preferably 2, % by volume, each relative to the total amount of gas. This can be achieved by cooling the hydrogen chloride, whereby the chlorinated hydrocarbons are condensed more or less, depending on the intensity of cooling.

The following examples illustrate the invention.

COMPARATIVE EXAMPLE

A gas stream consisting of 6.9 mol/h of HCl, 5.8 mol/h of CH$_3$OH and 0.29 mol/h of CCl$_4$ is reacted in the presence of a commercial aluminum oxide catalyst having a specific surface of 200 m$^2$/g. The catalyst is in a nickel tube having a diameter of 50 mm, which is heated from the outside by a stove. The length of the catalyst packing in this tube is 400 mm, the maximal temperature of the catalyst is 420° C. The excess HCl and the reaction products leave the reactor in gaseous form.

After 52.5 hours the selectivity of the reaction $$CH_3OH + HCl \rightarrow CH_3Cl + H_2O$$

Which had been 94.5%, begins to decrease considerably. After a further 64.5 hours it has fallen to 23.5%. After the test is stopped, large amounts of carbon are detected which had precipitated in the reactor.

EXAMPLE

When operating under the same conditions as in the Comparative Example, but with addition of 0.17 mol/h of oxygen to a gas current of 6.9 mol/h of HCl, 5.7 mol/h of CH$_3$OH and 0.29 mol/h of CCl$_4$, a substantial decrease of selectivity is not observed even after 150 hours. The precipitation of carbon is reduced by a factor of 14 as compared to the Comparative Example.

What is claimed is:

1. In a catalytic process for the manufacture of methyl chloride by a gaseous phase metathetical reaction of methanol and hydrogen chloride at elevated temperature and a pressure of at least 1 bar in the absence of metals of variable valency, the improvement which comprises reacting said methanol and hydrogen chloride in the presence of an aluminum oxide catalyst and an effective amount of oxygen or oxygen-containing gas in an amount of 1 to 80 liters of oxygen, as measured relative to 20° C. and 1 bar, per kilogram methanol wherein the useful life of said catalyst is increased and carbon precipitation is decreased.

2. The process of claim 1 wherein 0.75 to 1 mole of methanol is reacted per mole hydrogen chloride.

3. The process of claim 1 wherein said reaction is conducted in the presence of 1 to 50 liters of oxygen, as measured relative to 20° C. and 1 bar.

4. The process of claim 1 wherein said reaction is conducted in the presence of 1 to 30 liters of oxygen, as measured relative to 20° C. and 1 bar.